United States Patent
Hirakawa

(10) Patent No.: US 10,939,800 B2
(45) Date of Patent: *Mar. 9, 2021

(54) EXAMINATION SUPPORT DEVICE, EXAMINATION SUPPORT METHOD, AND EXAMINATION SUPPORT PROGRAM

(71) Applicant: FUJIFILM Corporation, Tokyo (JP)

(72) Inventor: Shinnosuke Hirakawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 62 days.

This patent is subject to a terminal disclaimer.

(21) Appl. No.: 16/453,701

(22) Filed: Jun. 26, 2019

(65) Prior Publication Data

US 2020/0029789 A1 Jan. 30, 2020

(30) Foreign Application Priority Data

Jul. 26, 2018 (JP) .............................. JP2018-140044

(51) Int. Cl.
| | |
|---|---|
| *A61B 1/00* | (2006.01) |
| *A61B 1/04* | (2006.01) |
| *A61B 1/267* | (2006.01) |
| *H04N 13/271* | (2018.01) |
| *H04N 5/232* | (2006.01) |
| *A61B 17/24* | (2006.01) |
| *H04N 5/225* | (2006.01) |

(52) U.S. Cl.
CPC ............ *A61B 1/00009* (2013.01); *A61B 1/04* (2013.01); *A61B 1/2676* (2013.01); *A61B 17/24* (2013.01); *H04N 5/23293* (2013.01); *H04N 13/271* (2018.05); *H04N 2005/2255* (2013.01)

(58) Field of Classification Search
CPC ..... A61B 1/00009; A61B 1/04; A61B 1/2676; A61B 17/24; A61B 5/7425; A61B 5/065; A61B 1/0005; H04N 13/271; H04N 5/23293; H04N 2005/2255
See application file for complete search history.

(56) References Cited

U.S. PATENT DOCUMENTS

| | | | |
|---|---|---|---|
| 2015/0057498 A1 | 2/2015 | Akimoto et al. | |
| 2020/0019813 A1* | 1/2020 | Hirakawa | ............... G06T 11/40 |

FOREIGN PATENT DOCUMENTS

| | | |
|---|---|---|
| JP | 2003-265408 A | 9/2003 |
| JP | 5718537 B2 | 5/2015 |

* cited by examiner

*Primary Examiner* — Diane D Mizrahi
(74) *Attorney, Agent, or Firm* — Studebaker & Brackett PC

(57) ABSTRACT

An image acquisition unit acquires a first medical image in a first expression form and a second medical image in a second expression form different from the first expression form. In a case where a conversion unit converts the first expression form of the first medical image and the second expression form of the second medical image into a third expression form, a converted first medical image and a converted second medical image are acquired. A similarity calculation unit calculates similarity between the converted first medical image and the converted second medical image.

9 Claims, 10 Drawing Sheets

EXAMINATION SUPPORT DEVICE, EXAMINATION SUPPORT METHOD, AND EXAMINATION SUPPORT PROGRAM

CROSS REFERENCE TO RELATED APPLICATIONS

The present application claims priority under 35 U.S.C. § 119 to Japanese Patent Application No. 2018-140044 filed on Jul. 26, 2018. The above application is hereby expressly incorporated by reference, in its entirety, into the present application.

BACKGROUND

Technical Field

The present disclosure relates to an examination support device, an examination support method, and an examination support program for supporting an examination of a tubular structure such as bronchi using an endoscope or the like.

Related Art

In recent years, a technique of observing or treating a tubular structure such as the large intestine or bronchi of a patient using an endoscope has been attracting attention. However, an endoscopic image is an image in which the color and the texture of the inside of a tubular structure are clearly expressed by an imaging element such as a charge coupled device (CCD) whereas the inside of a tubular structure is shown in a two-dimensional image. For this reason, it is difficult to grasp which position within the tubular structure is represented by the endoscopic image. Particularly, an endoscope for bronchi has a small diameter and a narrow visual field, and therefore, it is difficult to make a distal end of the endoscope reach a target position.

A method for previously acquiring a route to a target point within the tubular structure using a three-dimensional image acquired through tomography in accordance with a modality of a computed tomography (CT) device, a magnetic resonance imaging (MRI) device, or the like, generating a virtual endoscopic image, which is similar to an image actually photographed using an endoscope, from the three-dimensional image, and navigating the route of the endoscope to the target point using the virtual endoscopic image has been proposed. For example, JP5718537B has proposed a method for acquiring route information representing a route of a tubular structure from a three-dimensional image, generating a large number of virtual endoscopic images along the route, matching the virtual endoscopic images with actual endoscopic images which are acquired through imaging using an endoscope, and specifying a virtual endoscopic image at a current position of the endoscope to specify a distal end position of the endoscope.

However, even in a case where the navigation image is used, in a case of a structure having routes, such as bronchi, which are branched in multi-stages, a skilled technique is required for making a distal end of an endoscope reach a target position within a short period of time.

For this reason, a method for converting the intensity of the virtual endoscopic images into a gray scale and matching the actual endoscopic images with the virtual endoscopic images which have been converted into the gray scale to specify a distal end position of the endoscope is proposed (refer to JP2003-265408A).

On the other hand, since an endoscope is inserted into a tubular structure, in some cases, body fluid may adhere to a lens at a distal end of the endoscope or the lens may become cloudy due to the influence of mucus in the body. In addition, in some cases, an object that cannot be captured through tomographic imaging may be contained in an actual endoscopic image. In a case where an object or the like that cannot be captured due to cloudiness of a lens or through tomographic imaging is contained in an actual endoscopic image in this manner as noise, even if a virtual endoscopic image is converted into a gray scale, it is impossible to accurately match the actual endoscopic image with the virtual endoscopic image. As a result, it is impossible to accurately specify a distal end position of the endoscope.

SUMMARY OF THE INVENTION

The present disclosure has been made in consideration of the above-described circumstances, and an object of the present disclosure is to accurately match an actual endoscopic image with a virtual endoscopic image.

An examination support device according to the present disclosure comprises: an image acquisition unit that acquires a first medical image in a first expression form and a second medical image in a second expression form different from the first expression form; a conversion unit that acquires a converted first medical image and a converted second medical image by converting the first expression form of the first medical image and the second expression form of the second medical image into a third expression form; and a similarity calculation unit that calculates similarity between the converted first medical image and the converted second medical image.

The "expression form" means, so to speak, a style of an image which affects an impression of an image with respect to a viewer in a case where the image is displayed. For example, in a case where a medical image is acquired by actually performing imaging, the expression form of the medical image is an actual photo style. In addition, in a case where a medical image is generated through computer graphics (CG), the expression form of the medical image is a CG style. In addition, in a case where a medical image is generated by projecting a three-dimensional image using a projection method such as volume rendering, the expression form of the medical image is a CG style and becomes a volume rendered image style. Furthermore, in a case where a medical image is an actual endoscopic image, the medical image is an actual photo style and an actual endoscopic image style. Among actual endoscopic images, a medical image photographed through narrow band light observation becomes a narrow band light style, and a medical image photographed by white light observation becomes a white light style. In a case where the medical image is a virtual endoscopic image, the medical image is a CG style and a virtual endoscopic image style. Each of the expression forms is determined by the characteristics such as a range of parameters relating to gradation and color expression of an image, texture expression (asperity, fineness, a noise amount, and noise characteristics of an image), surface reflectance, and transparency, but the present invention is not limited thereto.

In the examination support device according to the present disclosure, the first medical image may be an actual image acquired by imaging a subject, and the second medical image may be an image generated from an image acquired by imaging the subject through a method different from that of the actual image.

In addition, in the examination support device according to the present disclosure, the first medical image may be an actual endoscopic image which is generated using an endoscope inserted into a tubular structure of the subject and represents an inner wall of the tubular structure, the second medical image may be a virtual endoscopic image which is generated from a three-dimensional image including the tubular structure of the subject and spuriously represents the inner wall of the tubular structure, the converted first medical image may be a first depth image representing a distance to the inner wall of the tubular structure from a viewpoint of the first medical image, and the converted second medical image may be a second depth image representing a distance to the inner wall of the tubular structure from a viewpoint of the second medical image.

The examination support device according to the present disclosure may further comprise: a position estimation unit that estimates a position of the endoscope in the tubular structure using the virtual endoscopic image of which the calculated similarity is greater than or equal to a predetermined threshold value.

In addition, in the examination support device according to the present disclosure, the position estimation unit may estimate the position of the endoscope in the tubular structure based on the difference in pixel values between the first depth image and the second depth image.

The examination support device according to the present disclosure may further comprise: a display control unit that displays the first depth image and the second depth image corresponding to the estimated position of the endoscope on a display unit.

In addition, the examination support device according to the present disclosure may further comprise a virtual endoscopic image generation unit generating the virtual endoscopic image from the three-dimensional image.

An examination support method according to the present disclosure comprises: acquiring a first medical image in a first expression form and a second medical image in a second expression form different from the first expression form; acquiring a converted first medical image and a converted second medical image by converting the first expression form of the first medical image and the second expression form of the second medical image into a third expression form; and calculating similarity between the converted first medical image and the converted second medical image.

There may be a program for causing a computer to execute the examination support method according to the present disclosure.

Another examination support device according to the present disclosure comprises: a memory which stores an instruction for causing a computer to execute; and a processor configured to execute the stored instruction, in which the processor acquires a first medical image in a first expression form and a second medical image in a second expression form different from the first expression form, acquires a converted first medical image and a converted second medical image by converting the first expression form of the first medical image and the second expression form of the second medical image into a third expression form, and calculates similarity between the converted first medical image and the converted second medical image.

According to the present disclosure, a first medical image in a first expression form and a second medical image in a second expression form different from the first expression form are acquired. The expression forms of the first medical image and the second medical image are converted into third expression forms and a converted first medical image and a converted second medical image are acquired. Furthermore, similarity between the converted first medical image and the converted second medical image are calculated. For this reason, even in a case where noise is contained in the first medical image and the second medical image, it is possible to cancel the noise in a case of converting the expression forms into third expression forms. Accordingly, according to the present disclosure, it is possible to accurately calculate the similarity between the first medical image and the second medical image.

DETAILED DESCRIPTION

Figure 1:
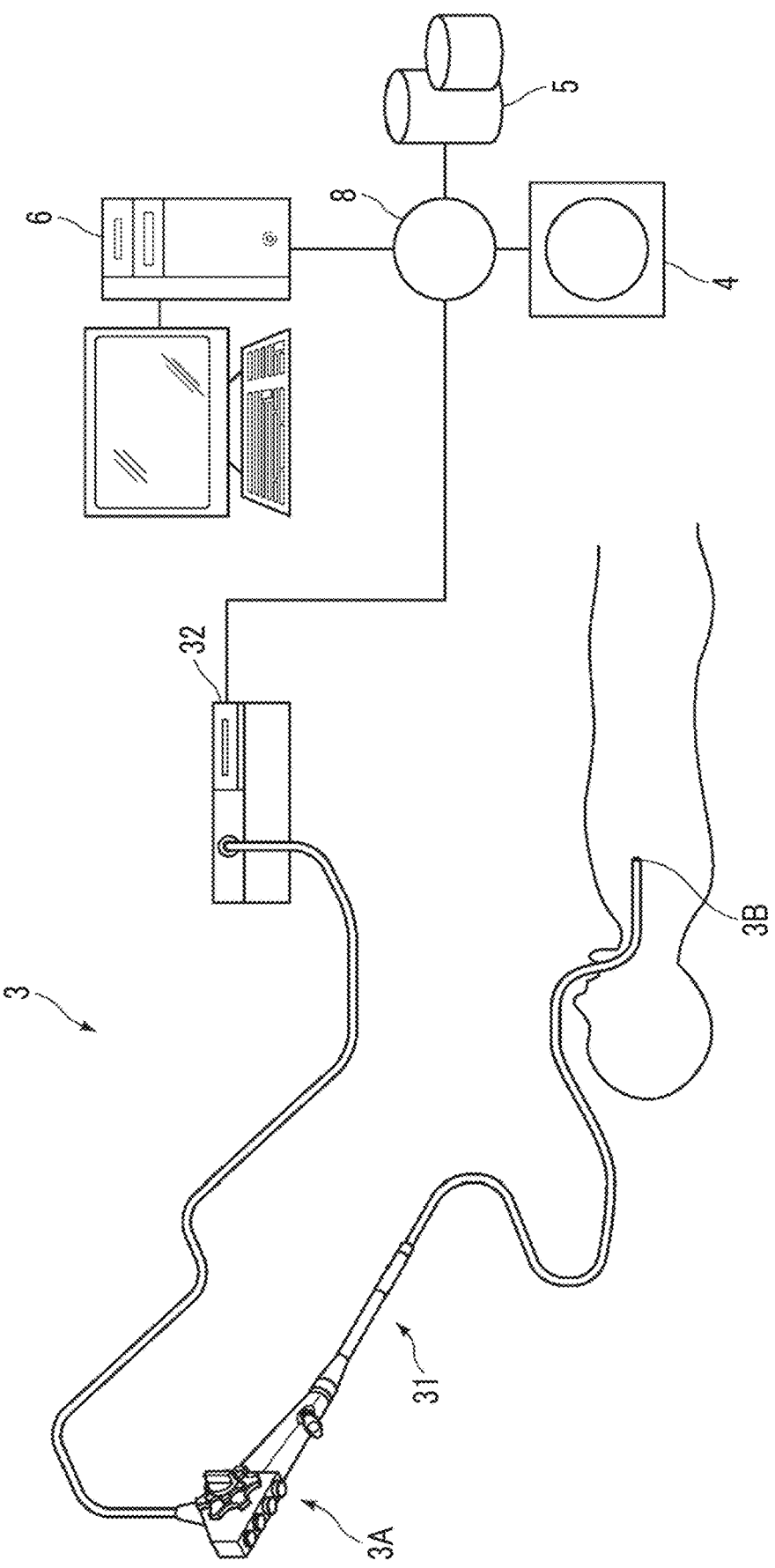
FIG. 1 is a hardware configuration diagram showing an outline of a diagnosis support system to which an examination support device according to an embodiment of the present disclosure is applied.

Hereinafter, an embodiment of the present disclosure will be described with reference to the drawings. FIG. 1 is a hardware configuration diagram showing an outline of a diagnosis support system to which an examination support device according to the present embodiment is applied. As shown in FIG. 1, an endoscope device 3, a three-dimensional image photographing device 4, an image storage server 5, and an examination support device 6 are connected to each other in a communicable state via a network 8 in the system of the present embodiment.

The endoscope device 3 comprises an endoscopic scope 31 imaging the inside of a tubular structure of a subject and a processor device 32 generating an image of the inside of the tubular structure based on a signal obtained through imaging.

An insertion portion of the endoscopic scope 31 to be inserted into the tubular structure of the subject is continuously attached to an operation portion 3A. The endoscopic scope 31 is connected to the processor device 32 via a universal cord which is attachably and detachably connected to the processor device 32. The operation portion 3A includes various buttons for instructing an operation such that a distal end 3B of the insertion portion is curved in the vertical direction and the horizontal direction within a predetermined angular range or for collecting a sample of tissue by operating a puncture needle attached to a distal end of the endoscopic scope 31. In the present embodiment, the endoscopic scope 31 is a flexible endoscope for bronchi and is inserted into a bronchus of a subject. Then, light guided by an optical fiber from a light source device which is not shown in the drawing and is provided in the processor device 32 is emitted from the distal end 3B of the insertion portion of the endoscopic scope 31, and an image within the bronchus of the subject is obtained using an imaging optical system of the endoscopic scope 31. The distal end 3B of the insertion portion of the endoscopic scope 31 will be referred to as an endoscope distal end 3B in the following description for ease of the description.

The processor device 32 generates an endoscopic image T0 by converting an imaging signal imaged using the endoscopic scope 31 into a digital image signal and by correcting the quality of the image through digital signal processing such as white balance adjustment and shading correction. The generated image is a color moving image represented, for example, by a predetermined sampling rate such as 30 fps, and one frame of the moving image becomes the endoscopic image T0. The endoscopic image T0 is sequentially transmitted to the image storage server 5 or the examination support device 6. Here, in the following description, the endoscopic image T0 photographed using the endoscope device 3 is referred to as an actual endoscopic image T0 in order to distinguish it from a virtual endoscopic image to be described below.

The three-dimensional image photographing device 4 is a device generating a three-dimensional image V0 representing an examination target site of the subject by imaging the site, and specific examples thereof include a CT device, which is used for imaging through a method other than the method for imaging the tubular structure into which the endoscopic scope 31 is inserted, an MRI device, a positron emission tomography (PET) device, and an ultrasound diagnostic apparatus. The three-dimensional image V0 generated by this three-dimensional image photographing device 4 is transmitted to and stored in the image storage server 5. In the present embodiment, the three-dimensional image photographing device 4 generates the three-dimensional image V0 obtained by imaging the chest including bronchi. In the present embodiment, the three-dimensional image photographing device 4 is a CT device, but the present invention is not limited thereto.

The image storage server 5 is a computer storing and managing various kinds of data and comprises a large-capacity external storage device and software for managing a database. The image storage server 5 communicates with other devices via the network 8 to transmit and receive image data or the like. Specifically, image data pieces such as the actual endoscopic image T0 acquired by the endoscope device 3 and the three-dimensional image V0 generated by the three-dimensional image photographing device 4 are acquired via the network, and the image data pieces are stored in a recording medium such as the large-capacity external storage device and are managed. The actual endoscopic image T0 is a moving image. For this reason, the actual endoscopic image T0 is preferably transmitted to the examination support device 6 without passing through the image storage server 5. The storage form of image data or the communication between the devices via the network 8 is based on protocols such as digital imaging and communication in medicine (DICOM).

The examination support device 6 is prepared by installing the examination support program of the present disclosure in one computer. The computer may be a workstation or a personal computer which is directly operated by a doctor performing a diagnosis, or may be a server computer which is connected to the workstation or the personal computer via a network. The examination support program is distributed by being recorded in a recording medium such as a digital versatile disc (DVD) or a compact disk read only memory (CD-ROM) and is installed in a computer from the recording medium. Alternatively, the examination support program is installed by being stored in a storage device of a server computer connected to a network or in network storage in an accessible state from the outside and by being downloaded in the computer used by a doctor who is an operator of the examination support device 6 as necessary.

Figure 2:
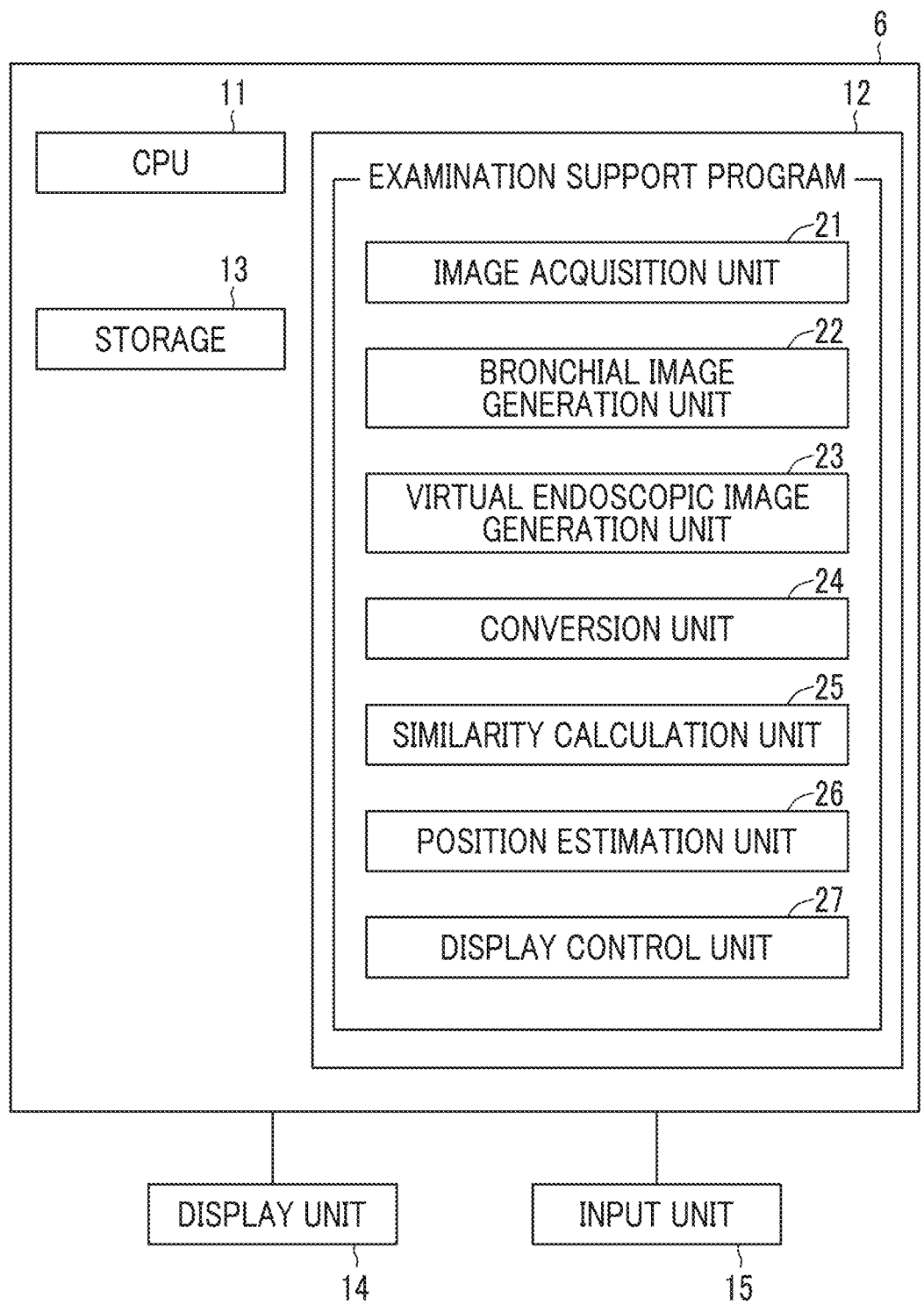
FIG. 2 is a view showing a schematic configuration of the examination support device realized by installing an examination support program in a computer.

FIG. 2 is a view showing a schematic configuration of the examination support device realized by installing an examination support program in a computer. As shown in FIG. 2, the examination support device 6 comprises a central processing unit (CPU) 11, a memory 12, and a storage 13 as a standard workstation configuration. In addition, a display unit 14 and an input unit 15 such as a mouse are connected to the examination support device 6. The display unit 14 includes a liquid crystal display or the like.

The storage 13 includes a hard disk drive or the like and stores the actual endoscopic image T0 and the three-dimensional image V0 acquired from the endoscope device 3, the three-dimensional image photographing device 4, the image storage server 5, and the like via the network 8, images (for example, virtual endoscopic images to be described below) generated through processing performed in the examination support device 6, various pieces of information required for the processing, and the like.

In addition, the examination support program is stored in the memory 12. As processing to be executed by the CPU 11, the examination support program defines: image acquisition processing for acquiring image data pieces such as the actual endoscopic image T0 generated by the processor device 32, the three-dimensional image V0 generated in the three-dimensional image photographing device 4, and a virtual endoscopic image generated as will be described below; bronchial image generation processing for generating a three-dimensional bronchial image B0 representing a bronchial graph structure from the three-dimensional image V0; virtual endoscopic image generation processing for generating a virtual endoscopic image from the three-dimensional image V0; conversion processing for acquiring a first depth image corresponding to an actual endoscopic image and a second depth image corresponding to a virtual endoscopic image by converting an expression form of the actual endoscopic image and an expression form of the virtual endoscopic image into expression forms of depth images, respectively; similarity calculation processing for calculating similarity between the first depth image and the second depth image; position estimation processing for estimating the position of the endoscope distal end 3B in bronchi using the virtual endoscopic image of which the calculated similarity is greater than or equal to a predetermined threshold value; and display control processing for displaying the positions or the like of the actual endoscopic image T0, the virtual endoscopic image, the bronchial image B0, and a specified endoscope distal end 3B on the display unit 14.

In a case where the CPU 11 performs these kinds of processing in accordance with the program, the computer as the examination support device 6 functions as an image acquisition unit 21, a bronchial image generation unit 22, a virtual endoscopic image generation unit 23, a conversion unit 24, a similarity calculation unit 25, a position estimation unit 26, and a display control unit 27.

The image acquisition unit 21 acquires the three-dimensional image V0 and the actual endoscopic image T0 which is obtained by imaging the inside of a bronchus at a predetermined viewpoint position using the endoscope device 3. The image acquisition unit 21 may acquire a three-dimensional image V0 and an actual endoscopic image T0 from the storage 13 in a case where the three-dimensional image V0 and the actual endoscopic image T0 are already stored in the storage 13. The actual endoscopic image T0 is an image representing the inner surface of a bronchus, that is, the inner wall of a bronchus. The actual endoscopic image T0 is displayed on the display unit 14 by being output to the display control unit 27. In addition, as will be described below, the image acquisition unit 21 acquires a virtual endoscopic image K0, which is generated by the virtual endoscopic image generation unit 23 and stored in the storage 13, from the storage 13.

The bronchial image generation unit 22 generates the three-dimensional bronchial image B0 by extracting a structure of bronchi from the three-dimensional image V0. Specifically, the bronchial image generation unit 22 extracts a graph structure of a bronchial region included in the input three-dimensional image V0 as the three-dimensional bronchial image B0, for example, through a method disclosed in JP2010-220742A. Hereinafter, an example of this method for extracting a graph structure will be described.

In the three-dimensional image V0, a pixel in the inside of bronchi corresponds to an air region, and therefore, is represented as a region showing a low pixel value. The bronchial wall is represented as a cylindrical or linear structure showing a comparatively high pixel value. The bronchi are extracted through analyzing the structure of the shape based on distribution of pixel values for each pixel.

The bronchi are branched in multi-stages, and the diameter of a bronchus decreases toward a terminal. The bronchial image generation unit 22 generates a plurality of three-dimensional images having different resolutions by performing multiple resolution conversion on the three-dimensional image V0 so as to detect the bronchi having different sizes, and applies a detection algorithm for each three-dimensional image with each resolution.

First, a Hessian matrix of each pixel of the three-dimensional image at each resolution is calculated and it is determined whether the pixel is within a tubular structure from a magnitude relation of an eigenvalue of the Hessian matrix. The Hessian matrix is a matrix having a second order partial differential coefficient of a density value in each axial (an x-axis, a y-axis, and a z-axis of the three-dimensional image) direction as an element, and becomes 3×3 matrix as shown in the following formula.

$$\nabla^2 I = \begin{bmatrix} I_{xx} & I_{xy} & I_{xz} \\ I_{xx} & I_{xy} & I_{xz} \\ I_{xx} & I_{xy} & I_{xz} \end{bmatrix} I_{xx} = \frac{\delta^2 I}{\delta x^2}, I_{xy} = \frac{\delta^2 I}{\delta x \delta y^2}, \ldots$$

In a case where eigenvalues of a Hessian matrix at any pixels are set as $\lambda 1$, $\lambda 2$, and $\lambda 3$, in a case where two eigenvalues among eigenvalues are large and one eigenvalue is close to 0, for example, in a case where $\lambda 3, \lambda 2 >> \lambda 1, \lambda 1 \cong 0$ is satisfied, it is known that the pixels are tubular structures. In addition, an eigenvector corresponding to the minimum eigenvalue ($\lambda 1 \cong 0$) of the Hessian matrix coincides with a principal axis direction of the tubular structure.

The bronchi can be represented by a graph structure. However, the tubular structures extracted in this manner is not limited to be detected as a graph structure in which all of tubular structures are connected to each other due to an influence of tumor or the like. Whether a plurality of tubular structures are connected to each other is determined by evaluating whether or not each of the extracted tubular structures is within a certain distance and whether or not an angle formed by a principal axis direction of each tubular structure and the direction of a basic line connecting predetermined points on two extracted tubular structures is within a certain angle, after the detection of the tubular structures from the entirety of the three-dimensional image V0 has been completed. Then, the connection relation of the extracted tubular structures is reconstructed. The extraction of the graph structure of bronchi is completed through the reconstruction.

Figure 3:
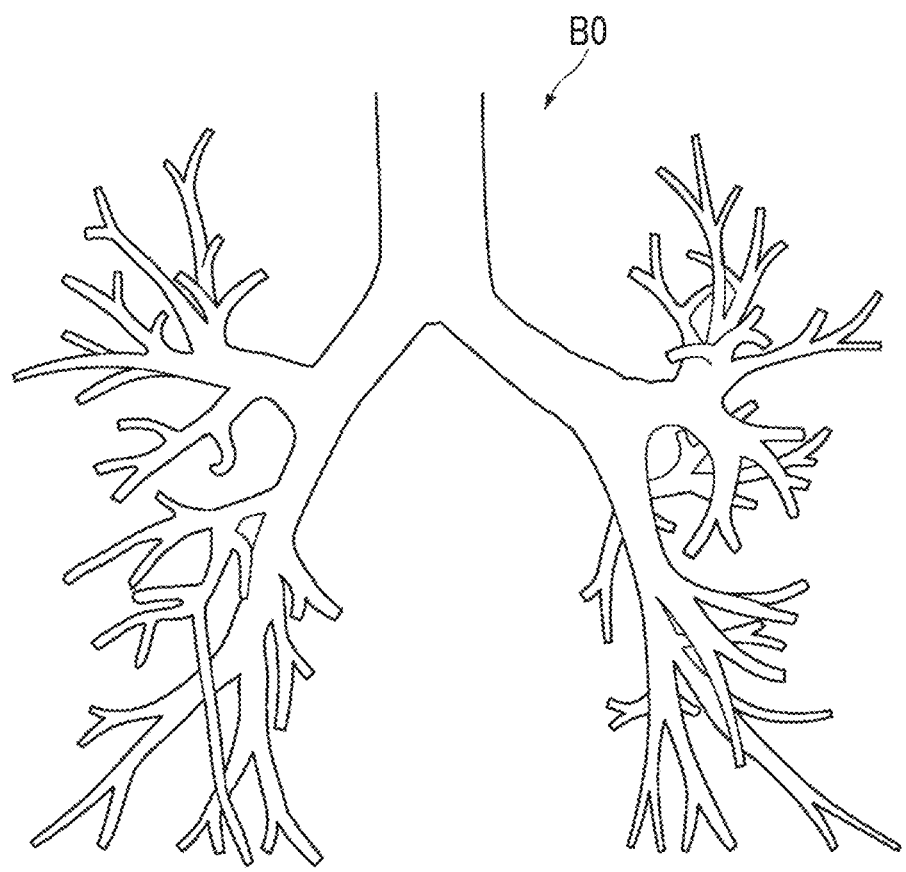
FIG. 3 is a view showing a bronchial image.

The bronchial image generation unit 22 can obtain a three-dimensional graph structure representing bronchi as the bronchial image B0 by classifying the extracted graph structure into a start point, an end point, a branch point, and a side and by connecting the start point, the end point, and the branch point by the side. FIG. 3 is a view showing a bronchial image B0. The method for generating the graph structure is not limited to the above-described method, and other methods may be employed.

The virtual endoscopic image generation unit 23 generates a virtual endoscopic image K0, which describes the inner wall of a bronchus and is viewed from a viewpoint of the inside of the three-dimensional image V0 corresponding to the viewpoint of the actual endoscopic image T0 in a target route in the bronchi. Hereinafter, the generation of the virtual endoscopic image K0 will be described.

Figure 4:
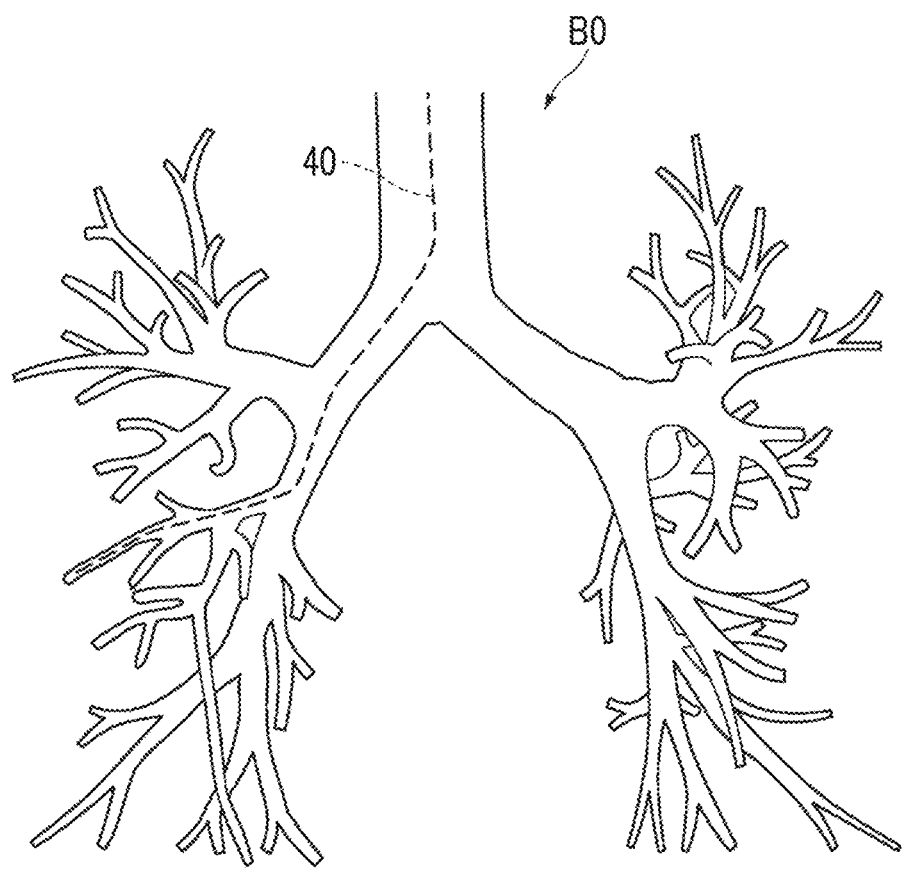
FIG. 4 is a view showing a bronchial image in which a route of an endoscope is set.

First, the virtual endoscopic image generation unit 23 acquires information of a predetermined route, into which the endoscope distal end 3B is to be inserted, in the bronchi. As the information of the route, for example, information of a bronchial image B0 designated by an operator using an input unit 15 after being displayed on the display unit 14 is used, but the present invention is not limited thereto. FIG. 4 shows a route 40 of an endoscope set in the bronchial image B0.

The virtual endoscopic image generation unit 23 generates a virtual endoscopic image K0 representing the inner wall of a bronchus at predetermined intervals along the route 40 within the bronchus represented by the acquired information of the route. The predetermined intervals may be, for example, 10 pixels on the route 40, but the present invention is not limited thereto.

The virtual endoscopic image generation unit 23 sets each position on the route 40 as viewpoints. Central projection of projecting the three-dimensional images V0 on a plurality of visual lines radially extended in the insertion direction (that is, the direction toward the terminal of a bronchus) of the endoscope distal end 3B from each set viewpoint on a predetermined projection surface is performed to generate a projection image. This projection image becomes the virtual endoscopic image K0 virtually generated as an image which is photographed at a distal end position of the endoscope. As a specific method of the central projection, it is possible to use, for example, a well-known volume rendering method. In addition, the view angle (the range of the visual lines) of the virtual endoscopic image K0 and the center of the visual field (center in the projection direction) are set in advance through input or the like performed by an operator. A plurality of generated virtual endoscopic images K0 are stored in the storage 13. In the present embodiment, since the three-dimensional image V0 is a CT image, the virtual endoscopic image K0 is a monochrome image represented by a CT value.

The conversion unit 24 converts an expression form of the actual endoscopic image T0 into an expression form of a depth image. In addition, the conversion unit converts an expression form of the virtual endoscopic image K0 generated by the virtual endoscopic image generation unit 23 into an expression form of a depth image. For this reason, the conversion unit 24 may use, for example, a method disclosed in "Atapour-Abarghouei, A. and Breckon, T. P. (2018) 'Real-time monocular depth estimation using synthetic data with domain adaptation.', 2018 IEEE Conference on Computer Vision and Pattern Recognition (CVPR). Salt Lake City, Utah, USA, 18-22 Jun. 2018." (hereinafter, referred to as Non-Patent Document 1). The method described in Non-Patent Document 1 is a method for converting an image into a depth image using a model such as a neural network that outputs the depth image in a case where the image is input. The model is generated by performing machine-learning using information representing various images and depths thereof as teaching data. A pixel value of the depth image represents a distance from a viewpoint position. Specifically, the pixel value of the depth image becomes lower as the distance from the viewpoint position increases, and as a result, the image becomes darker as the distance from the viewpoint position increases. It is possible to calculate the distance from the viewpoint position based on the pixel value of the depth image by previously setting the relationship between the distance and the pixel value of the depth image.

Figure 5:
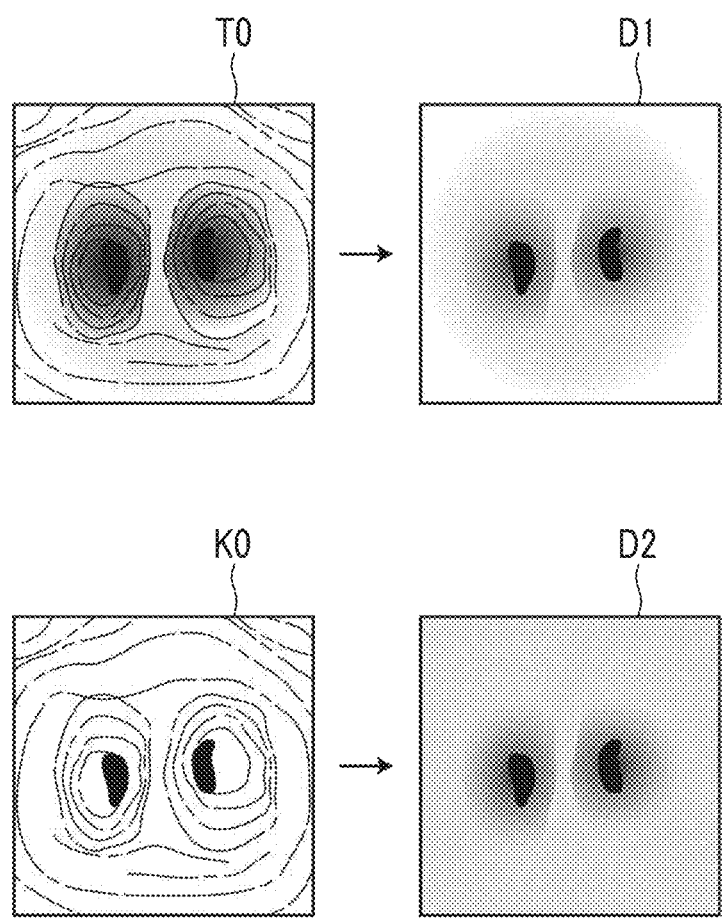
FIG. 5 is a diagram for illustrating conversion of a virtual endoscopic image.

The conversion unit 24 in the present embodiment comprises a model including a neural network or the like which is disclosed in Non-Patent Document 1 and machine-learned so as to convert an expression form of an image into an expression form of a depth image, as a converter. A well-known method can be used as a machine-learning method. For example, a support vector machine, a deep neural network, a convolutional neural network, and a recurrent neural network can be used. In the present embodiment, in a case where an object or the like that cannot be captured due to cloudiness of a lens or through tomographic imaging is contained in an actual endoscopic image T0 as noise, machine-learning is performed so as to convert the actual endoscopic image T0 into a depth image by removing the noise. In addition, a converter that converts expression forms of the actual endoscopic image T0 and the virtual endoscopic image K0 into expression forms of depth images through logical operation may be used. With such a converter, as shown in FIG. 5, the expression forms of the actual endoscopic image T0 and the virtual endoscopic image K0 are converted into the expression forms of the depth images, and as a result, a first depth image D1 corresponding to the actual endoscopic image T0 and a second depth image D2 corresponding to the virtual endoscopic image are acquired. In addition, noise, such as an object that cannot be captured due to cloudiness of a lens or through tomographic imaging, which is contained in the actual endoscopic image T0 is canceled by the conversion. The first depth image D1 and the second depth image D2 respectively correspond to the converted first medical image and the converted second medical image.

The actual endoscopic image T0 constitutes one frame of a moving image. For this reason, the conversion unit 24 converts expression forms of the actual endoscopic images T0, which have been sequentially acquired, into expression forms of depth images. In addition, the conversion unit 24 may previously convert all the virtual endoscopic images K0 generated by the virtual endoscopic image generation unit 23 into depth images. In addition, as will be described below, the virtual endoscopic images K0 around the position of an estimated endoscope distal end 3B may be converted into depth images every time the position estimation processing is performed. In the present embodiment, all the virtual endoscopic images K0 generated by the virtual endoscopic image generation unit 23 are converted into depth images. Accordingly, the acquired second depth image D2 is stored in the storage 13.

The similarity calculation unit 25 calculates similarity between the first depth image D1 and the second depth image D2 regarding the actual endoscopic images T0, which have been sequentially acquired, in order to estimate the position of the endoscope distal end 3B to be described below. It is possible to use a reciprocal of a sum of absolute values of differences in pixel values between pixels corresponding to the first depth image D1 and the second depth image D2, a reciprocal of a sum of squares of differences, or the like as the similarity.

The position estimation unit 26 estimates the position of the endoscope distal end 3B in bronchi using a virtual endoscopic image of which the similarity calculated by the similarity calculation unit 25 is greater than or equal to a predetermined threshold value Th1.

As described above, the actual endoscopic image T0 constitutes one frame of a moving image. For this reason, the similarity calculation unit 25 calculates similarity between the second depth image D2 and the first depth image D1 regarding a latest actual endoscopic image T0 among sequentially acquired actual endoscopic images T0 of the moving image. Here, in order to estimate the position of the endoscope distal end 3B, the similarity calculation unit 25 may calculate the similarity between the first depth image D1 and all the second depth images D2 generated from all the virtual endoscopic images K0 stored in the storage 13. However, the computational complexity becomes high. For this reason, in the present embodiment, the similarity is calculated as follows.

First, the similarity calculation unit 25 specifies a second depth image D2 which becomes a reference generated at a reference position in a bronchus as a reference depth image DB. Then, the similarity calculation unit calculates similarity between the reference depth image DB and a latest first depth image D1 among sequentially acquired first depth images D1. A second depth image D2 generated from a virtual endoscopic image having a position closest to the entrance of a bronchus in the route 40 of the bronchus as a viewpoint position may be used as the reference depth image DB. In a case where a first depth image D1 of which the similarity with the reference depth image DB is greater than or equal to a threshold value Th2 is acquired, the position estimation unit 26 estimates that the position of the endoscope distal end 3B is at the reference position. The threshold value Th2 may be the same as or different from the threshold value Th1.

Figure 6:
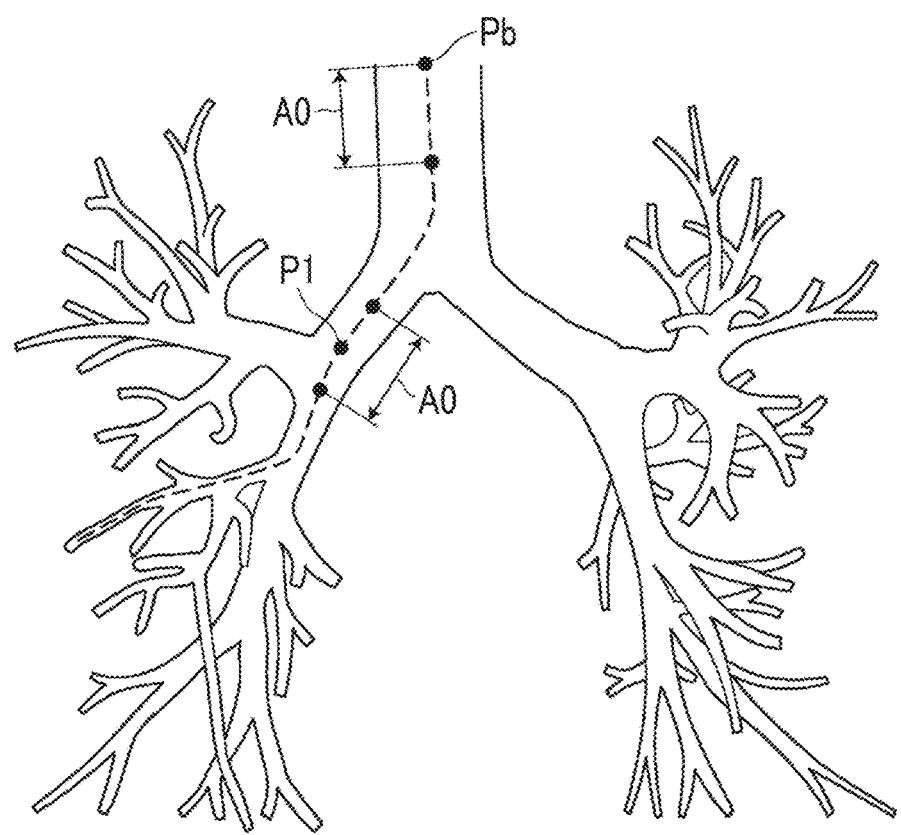
FIG. 6 is a diagram for illustrating a range of virtual endoscopic images for calculating the similarity.

In this manner, in a case where the position estimation unit 26 estimates that the position of the endoscope distal end 3B is at the reference position, the similarity calculation unit 25 calculates the similarity between the latest first depth image D1 and one or more second depth images D2 within a predetermined range A0 from the reference position Pb as shown in FIG. 6. In a case where it is estimated that the endoscope distal end 3B is at the position P1 as shown in FIG. 6 at a point in time when the endoscope distal end 3B moves into the bronchi and a certain actual endoscopic image T0 is acquired, the similarity calculation unit 25 calculates the similarity between the actual endoscopic image T0 and one or more second depth images D2 within the predetermined range A0 including the position P1, with respect to a first depth image D1 regarding an actual endoscopic image T0 acquired next. That is, since the actual endoscopic image T0 constitutes one frame of a moving image, the similarity calculation unit 25 calculates the similarity between the latest first depth image D1 and the second depth image D2 every time the actual endoscopic image T0 is acquired.

The position estimation unit 26 estimates that a position of a viewpoint at which a virtual endoscopic image K0 which corresponds to the second depth image D2 and has the largest similarity being greater than or equal to a threshold value Th1 among the similarities between the latest first depth image D1 and all the second depth images D2 within the range A0 is generated is a position of the endoscope distal end 3B.

Figure 7:
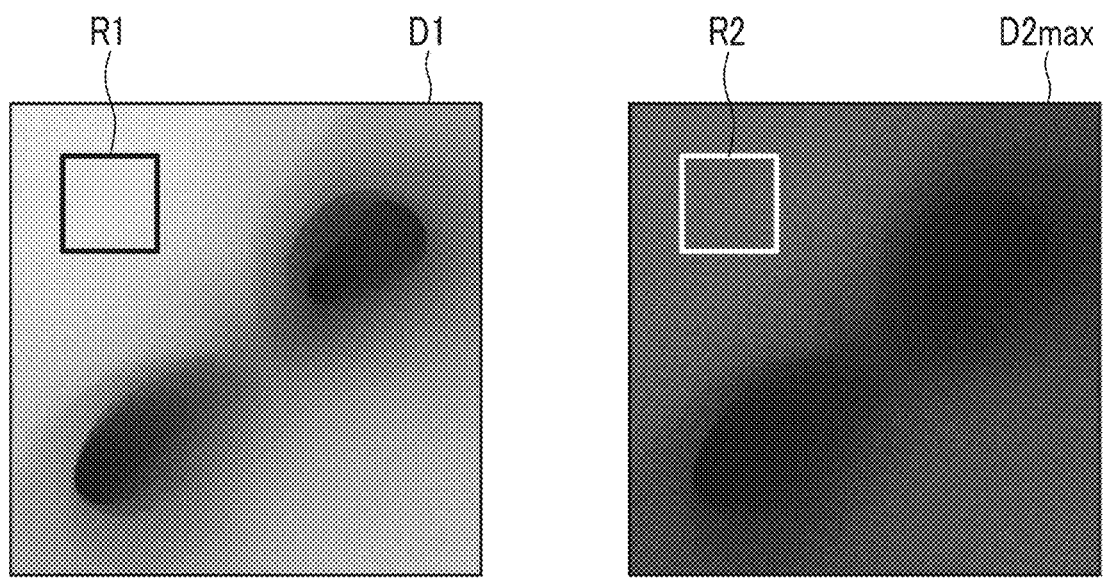
FIG. 7 is a diagram for illustrating estimation of a position of an endoscope distal end.

In the present embodiment, it is possible to estimate that the position in an advancing direction of the endoscope distal end 3B in the bronchi becomes more accurate using the first depth image D1 and the second depth image D2. FIG. 7 is a diagram for illustrating estimation of a position of an endoscope distal end 3B. As described above, in the depth image, a pixel value represents a distance in the depth direction. For this reason, the position estimation unit 26 sets regions R1 and R2 which respectively correspond to the first depth image D1 and a second depth image D2max having the largest similarity with the first depth image D1. Then, a representative value (for example, an average value, a median value, a maximum value) of pixel values in the region R1 is calculated, and the representative value is converted into a distance L1 from the viewpoint position. Similarly, a representative value (for example, an average value, a median value, a maximum value) of pixel values in the region R2 is calculated, and the representative value is converted into a distance L2 from the viewpoint position.

A difference ΔL between the distance L1 and the distance L2 which have been calculated in this manner represents a position deviation amount between the position of the endoscope distal end 3B and the position of a viewpoint at which a virtual endoscopic image K0 corresponding to the second depth image D2max having the maximum similarity is generated. Hereinafter, ΔL is also used as a reference numeral for the positional deviation amount. For example, in a case where the calculated distance L1 is 11 mm and the calculated distance L2 is 20 mm, the positional deviation amount ΔL is L2−L1=9 mm. The position estimation unit 26 corrects the position of the viewpoint, at which a virtual endoscopic image K0 corresponding to the second depth image D2 having the largest similarity is generated, based on the positional deviation amount ΔL calculated in this manner, and the corrected position is estimated as a position of the endoscope distal end 3B. For example, in a case where the positional deviation amount ΔL is 9 mm, the position of the viewpoint is corrected 9 mm forward (that is, in the insertion direction of the endoscope distal end 3B). In a case where the positional deviation amount becomes a negative value, the position estimation unit 26 corrects the position of the viewpoint backward (that is, in a direction in which the endoscope distal end 3B returns).

Figure 8:
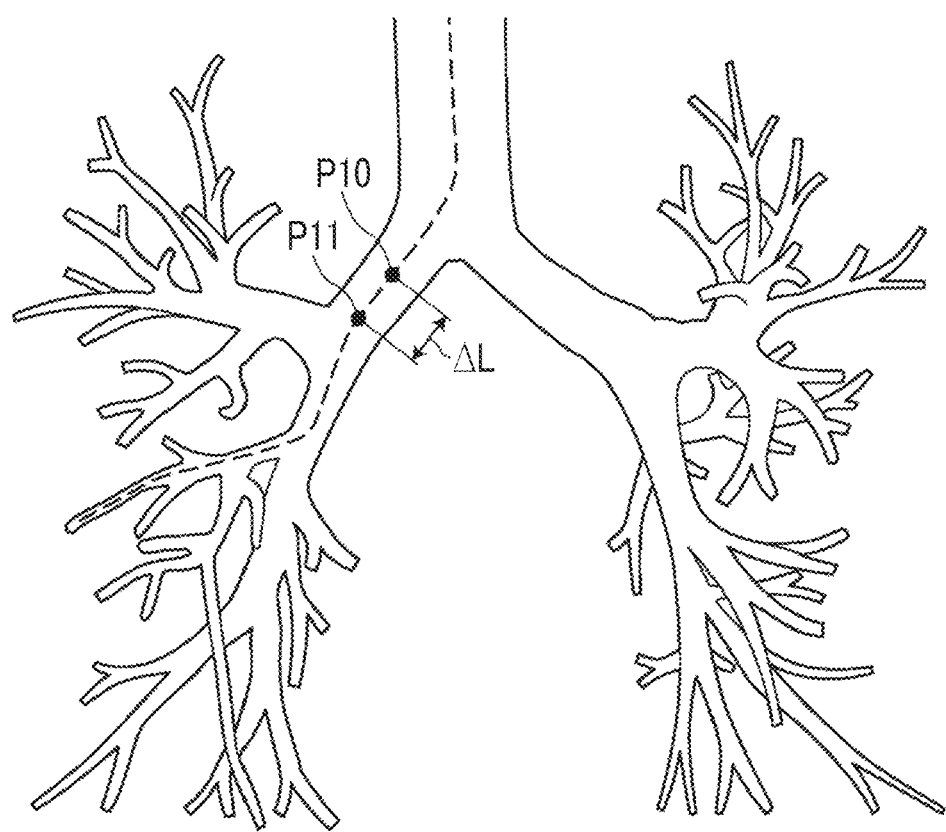
FIG. 8 is a diagram for illustrating correction of a position of a viewpoint.

FIG. 8 is a diagram for illustrating correction of a position of a viewpoint. As shown in FIG. 8, it is assumed that the position of the viewpoint at which the virtual endoscopic image K0 corresponding to the second depth image D2 having the largest similarity is generated is a position P10.

In addition, it is assumed that the positional deviation amount ΔL is a positive value. The position estimation unit 26 shifts the position P10 by the positional deviation amount ΔL in the advancing direction of the endoscope distal end 3B and estimates the position of the endoscope distal end 3B as a position P11.

The display control unit 27 displays a first depth image D1 and a second depth image D2 corresponding to the virtual endoscopic image K0 at the position of the endoscope distal end 3B on the display unit 14. The display control unit 27 may display a bronchial image B0 on the display unit 14 and perform display for specifying the endoscope distal end 3B in the displayed bronchial image B0. In addition, the actual endoscopic image T0 may be displayed instead of or in addition to the first depth image DE In addition, the virtual endoscopic image K0 may be displayed instead of or in addition to the second depth image D2.

Figure 9:
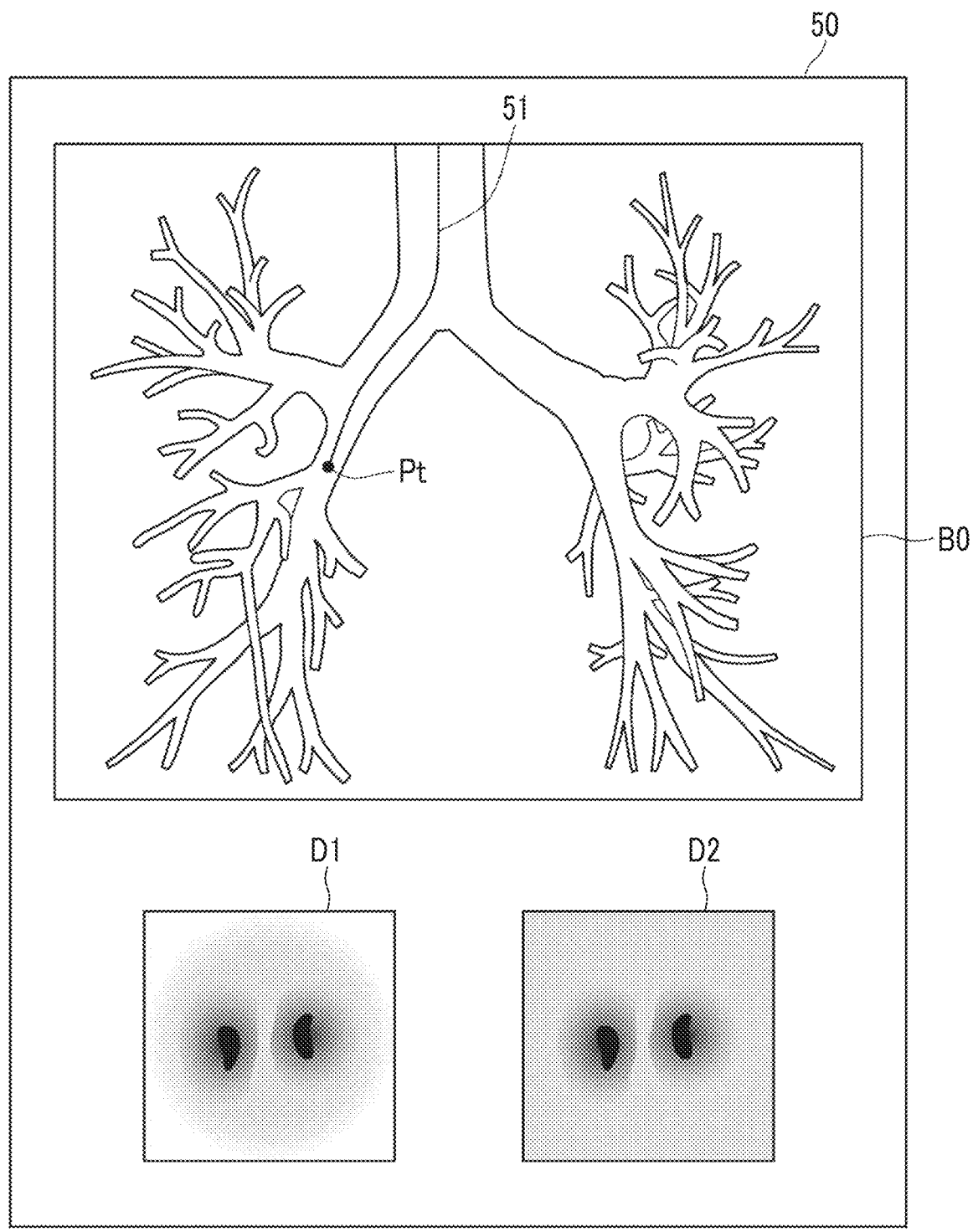
FIG. 9 shows a display image.

FIG. 9 is a view showing a display image of the display unit 14. As shown in FIG. 9, the first depth image D1, the second depth image D2 at the position of the endoscope distal end 3B, and the bronchial image B0 are displayed in a display image 50. A movement trajectory 51 of the endoscope and the position Pt of the endoscope distal end 3B are displayed in the bronchial image B0.

Figure 10:
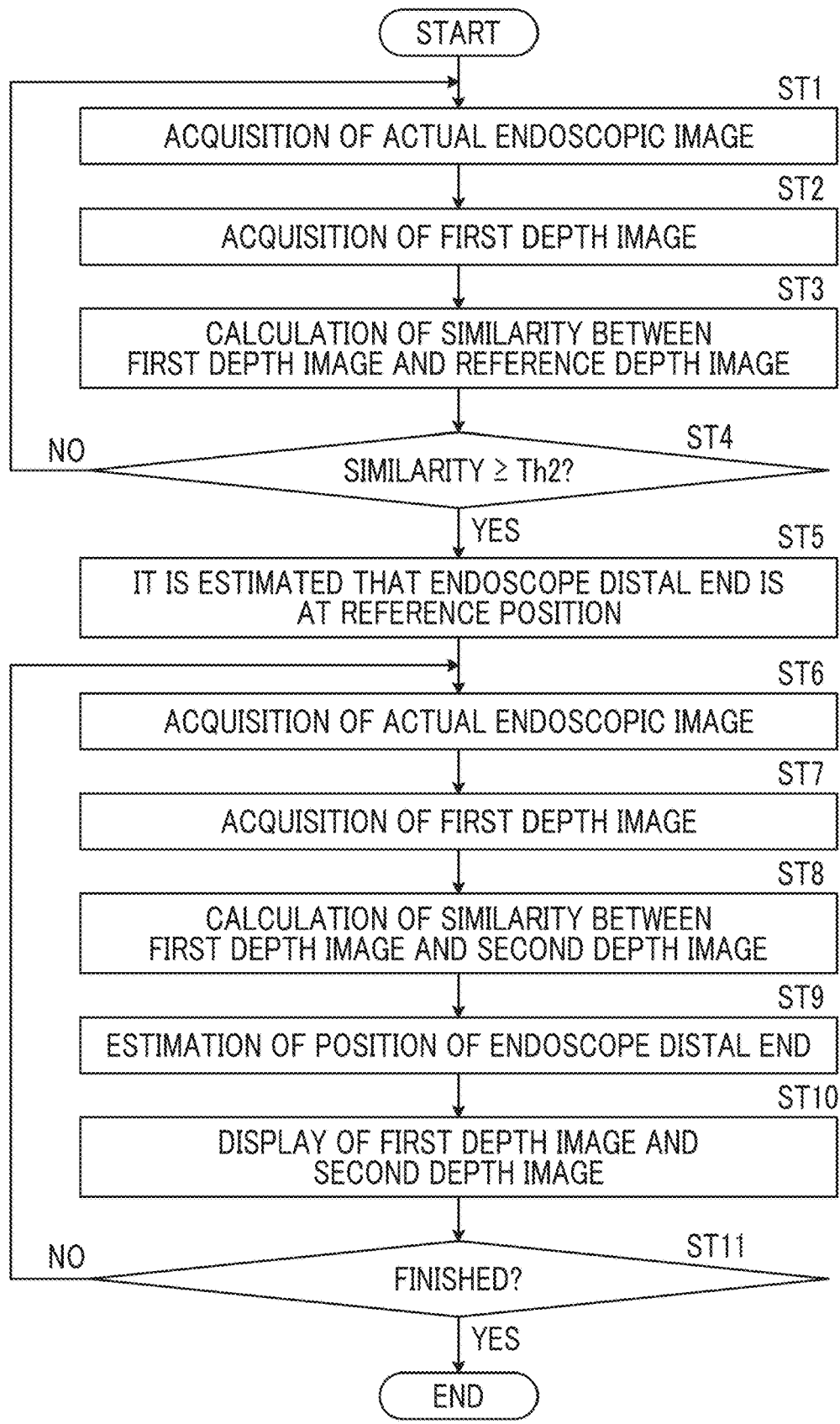
FIG. 10 is a flowchart showing processing performed in the present embodiment.

Next, processing performed in the present embodiment will be described. FIG. 10 is a flowchart showing processing performed in the present embodiment. The bronchial image B0 is generated by the bronchial image generation unit 22 and the virtual endoscopic image K0 is generated by the virtual endoscopic image generation unit 23. Furthermore, the second depth image D2 regarding the virtual endoscopic image K0 is generated by the conversion unit 24. These images are stored in the storage 13. In a case where the endoscope distal end 3B is inserted into a subject and an instruction to start an operation is input from the input unit 15, the image acquisition unit 21 acquires an actual endoscopic image T0 (Step ST1). Subsequently, the conversion unit 24 converts an expression form of the actual endoscopic image T0 into an expression form of a depth image to acquire the first depth image D1 (Step ST2). Then, the similarity calculation unit 25 calculates the similarity between the first depth image D1 and the reference depth image DB (Step ST3). Furthermore, the position estimation unit 26 determines whether the similarity calculated by the similarity calculation unit 25 is greater than or equal to the threshold value Th2 (step ST4). In a case where Step ST4 is negative, the process returns to Step ST1 and the processing from Step ST1 to Step ST4 is repeated.

In a case where Step ST4 is affirmed, the position estimation unit 26 estimates that the endoscope distal end 3B is at the reference position Pb (Step ST5). The image acquisition unit 21 subsequently acquires an actual endoscopic image T0 (Step ST6) and the conversion unit 24 converts an expression form of the actual endoscopic image T0 into an expression form of a depth image to acquire the first depth image D1 (Step ST7). Subsequently, the similarity calculation unit 25 calculates similarity between the first depth image D1 acquired in Step ST7 and a second depth image D2 corresponding to a virtual endoscopic images K0 within a predetermined range from a current position of the endoscope distal end 3B (Step ST8). Then, the position estimation unit 26 estimates that the position, at which the virtual endoscopic image K0 corresponding to the second depth image D2 having the largest similarity being greater than or equal to a threshold value Th1 is acquired, is a position of the endoscope distal end 3B (Step ST9). Subsequently, the display control unit 27 displays the first depth image D1 and the second depth image D2 (Step ST10). Then, the processing from Step ST6 to Step ST10 is repeated until an instruction to end the operation is issued (Step ST11: affirmation).

In the processing of the above-described embodiment, in some cases, there is no second depth image D2 of which the similarity is greater than or equal to the threshold value Th1. In such a case, the position of the endoscope distal end 3B may be estimated by, for example, expanding the range in which the second depth image D2 for calculating the similarity is acquired.

In the present embodiment, the expression forms of the actual endoscopic image T0 and the virtual endoscopic image K0 are converted into expression forms of depth images to obtain the first depth image D1 and the second depth image D2, and the similarity between the first depth image D1 and the second depth image D2 is calculated in this manner. For this reason, even in a case where an object or the like that cannot be captured due to cloudiness of a lens or through tomographic imaging is contained in an actual endoscopic image T0 as noise, it is possible to cancel noise in a case where the actual endoscopic image T0 is converted into an expression form of a depth image. Accordingly, according to the present embodiment, it is possible to accurately calculate the similarity between the actual endoscopic image T0 and the virtual endoscopic image K0. In addition, It is possible to accurately estimate the position of the endoscope distal end 3B using the similarity calculated in this manner.

Figure 11:
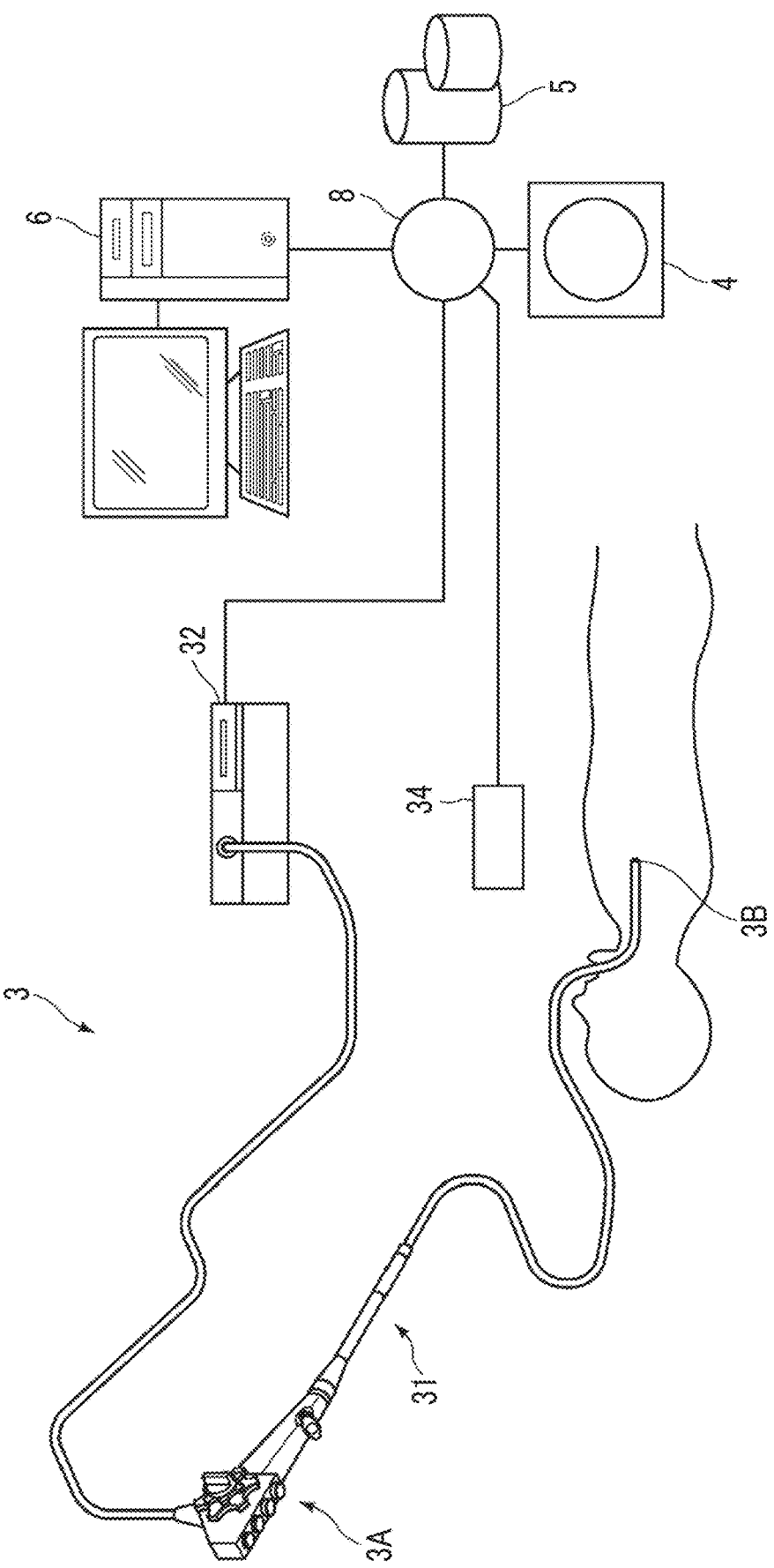
FIG. 11 is a hardware configuration diagram showing an outline of a diagnosis support system to which an examination support device according to another embodiment of the present disclosure is applied.

In the above-described embodiment, the position estimation unit 26 estimates the reference position of the endoscope distal end 3B, but the present invention is not limited thereto. For example, as shown in FIG. 11, the endoscope device 3 may be set to have a position detection device 34 and estimate the position of the endoscope distal end 3B by calculating the similarity between the first depth image D1 and the second depth image D2 while detecting the position of the endoscope distal end 3B using the position detection device 34.

In this case, the position detection device 34 detects the position and the direction of the endoscope distal end 3B in the body of the subject. Specifically, the position detection device 34 has an echo device having a detection region of a three-dimensional coordinate system in which the position of a specific site of the subject is used as a reference, and detects the relative position and direction of the endoscope distal end 3B in the body of the subject by detecting the characteristic shape of the endoscope distal end 3B using the echo device. Then, the information of the detected position and direction of the endoscope distal end 3B is output to the examination support device 6 as position information Q0 (for example, refer to JP2006-061274A). The detected position and direction of the endoscope distal end 3B respectively correspond to a viewpoint and a visual line direction of an actual endoscopic image T0 obtained through imaging. Here, the position of the endoscope distal end 3B is represented by three-dimensional coordinates in which the above-described position of a specific site of the subject is used as a reference. In addition, the position information Q0 is output to the examination support device 6 using the same sampling rate as that of the actual endoscopic image T0.

In the case where the position detection device 34 is used in this manner, the similarity calculation unit 25 calculates the similarity between the first depth image D1 and one or more second depth images D2 within a predetermined range A0 from the position of a bronchus represented by the position information Q0. Similarly to the above-described embodiment, the position estimation unit 26 estimates that a position at which a virtual endoscopic image K0 which corresponds to the second depth image D2 and has the largest similarity being greater than or equal to a threshold value Th1 among the similarities between the first depth image D1 and all the second depth images D2 within the range A0 is generated is a position of the endoscope distal end 3B. Even in this case, the estimated position may be corrected by obtaining the positional deviation amount based on pixel values of the first depth image D1 and the second depth image D2 similarly to the above-described embodiment.

In addition, in the above-described embodiment, the similarity calculation unit 25 calculates the similarity between the first depth image D1 and the second depth image D2 every time an actual endoscopic image T0 is acquired, but the present invention is not limited thereto. For example, it may be determined whether a branched structure of bronchi is included in an actual endoscopic image T0 through a method disclosed in JP2016-163609A, and the similarity between the first depth image D1 and the second depth image D2 may be calculated by acquiring the first depth image D1 only in a case where the branched structure of the bronchi is included in the actual endoscopic image T0.

In addition, in the above-described embodiment, the case where the examination support device of the present disclosure is applied for observing the bronchi has been described. However, the present disclosure is not limited thereto and can be applied even to a case of observing a tubular structure, such as the stomach, the large intestine, and blood vessels using an endoscope.

In addition, in the above-described embodiment, the positional deviation amount is calculated from pixel values of the first depth image D1 and the second depth image D2 to correct the position of the endoscope distal end 3B, but the present invention is not limited thereto. The position estimation unit 26 may estimate the viewpoint position of the virtual endoscopic image K0 estimated based on the similarity as a position of the endoscope distal end 3B as it is.

In addition, in the above-described embodiment, the examination support device 6 comprises the bronchial image generation unit 22 and the virtual endoscopic image generation unit 23, but the present invention is not limited thereto. The bronchial image generation unit 22 and the virtual endoscopic image generation unit 23 may be provided as separate devices from the examination support device 6. In this case, the bronchial image B0 and the virtual endoscopic image K0 are input to the examination support device 6 from the separate devices and are acquired by the image acquisition unit 21.

In addition, in the above-described embodiment, the expression forms of the actual endoscopic image T0 and the virtual endoscopic image K0 are converted into expression forms of depth images, but the present invention is not limited thereto. For example, the actual endoscopic image T0 and the virtual endoscopic image K0 may be converted into an expression form such as a CG style in addition to the expression forms of the depth images.

In addition, in the above-described embodiment, an actual endoscopic image is used as the first medical image and a virtual endoscopic image is used as the second medical image, but the present invention is not limited thereto. It is possible to use any medical images as long as expression forms of a first medical image and a second medical image are different from each other, for example, a case where the first medical image is set as a CT image and the second medical image is set as an MRI image.

In addition, in the above-described embodiment, the examination support device according to the present disclosure is applied to a device that supports endoscopic examination, but the present invention is not limited thereto. The present disclosure can be applied to any device that supports examination for acquiring a first medical image with a first expression form and a second medical image with a second expression form different from the first expression form.

In addition, in the above-described embodiment, it is possible to use, for example, various processors shown below as hardware structures of processing units such as the image acquisition unit 21, the bronchial image generation unit 22, the virtual endoscopic image generation unit 23, the conversion unit 24, the similarity calculation unit 25, the position estimation unit 26, and the display control unit 27 which execute various kinds of processing. A programmable logic device (PLD) which is a processor capable of changing a circuit configuration after manufacturing a field programmable gate array (FPGA) or the like and exclusive circuitry such as an application specific integrated circuit (ASIC) which is a processor having a circuit configuration exclusively designed to execute specific processing are included in the above-described various processors in addition to a CPU which is a general-purpose processor which executes software (program) to function as various processing units as described above.

One processing unit may be configured to include one processor among these various processors, or may be configured to include a combination of two or more same or different kinds of processors (for example, a combination of a plurality of FPGAs or a combination of a CPU or a FPGA). In addition, a plurality of processing units may constitute one processor.

An example in which a plurality of processing units constitute one processor first includes a form in which a combination of a software and one or more CPUs constitutes one processor so as to be represented by a computer of a client, a server, and the like so that this processor functions as a plurality of processing units. Another example in which a plurality of processing units constitute one processor second includes a form of using a processor in which a function of an entire system including a plurality of processing units is realized with one integrated circuit (IC) chip so as to be represented by system-on-chip (SoC) or the like. In this manner, the various processing units are configured using one or more of the above-described various processors as a hardware structure.

Furthermore, more specifically, it is possible to use circuitry, in which circuit elements such as semiconductor elements are combined, as the hardware structure of the various processors.

What is claimed is:

1. An examination support device comprising:
    an image acquisition unit that acquires a first medical image in a first expression form and a second medical image in a second expression form different from the first expression form;
    a conversion unit that acquires a converted first medical image and a converted second medical image by converting the first expression form of the first medical image and the second expression form of the second medical image into a third expression form; and
    a similarity calculation unit that calculates similarity between the converted first medical image and the converted second medical image.

2. The examination support device according to claim 1, wherein the first medical image is an actual image acquired by imaging a subject, and the second medical image is an image generated from an image acquired by imaging the subject through a method different from that of the actual image.

3. The examination support device according to claim 2, wherein the first medical image is an actual endoscopic image which is generated using an endoscope inserted into a tubular structure of the subject and represents an inner wall of the tubular structure,
    wherein the second medical image is a virtual endoscopic image which is generated from a three-dimensional image including the tubular structure of the subject and spuriously represents the inner wall of the tubular structure,
    wherein the converted first medical image is a first depth image representing a distance to the inner wall of the tubular structure from a viewpoint of the first medical image, and
    wherein the converted second medical image is a second depth image representing a distance to the inner wall of the tubular structure from a viewpoint of the second medical image.

4. The examination support device according to claim 3, further comprising:
    a position estimation unit that estimates a position of the endoscope in the tubular structure using the virtual endoscopic image of which the calculated similarity is greater than or equal to a predetermined threshold value.

5. The examination support device according to claim 4, wherein the position estimation unit estimates the position of the endoscope in the tubular structure based on the difference in pixel values between the first depth image and the second depth image.

6. The examination support device according to claim 4, further comprising:
    a display control unit that displays the first depth image and the second depth image corresponding to the estimated position of the endoscope on a display unit.

7. The examination support device according to claim 3, further comprising:
    a virtual endoscopic image generation unit generating the virtual endoscopic image from the three-dimensional image.

8. An examination support method comprising:
    acquiring a first medical image in a first expression form and a second medical image in a second expression form different from the first expression form;
    acquiring a converted first medical image and a converted second medical image by converting the first expression form of the first medical image and the second expression form of the second medical image into a third expression form; and
    calculating similarity between the converted first medical image and the converted second medical image.

9. A non-transitory computer-readable storage medium that stores an examination support program causing a computer to execute:
    a step of acquiring a first medical image in a first expression form and a second medical image in a second expression form different from the first expression form;
    a step of acquiring a converted first medical image and a converted second medical image by converting the first expression form of the first medical image and the second expression form of the second medical image into a third expression form; and a step of calculating similarity between the converted first medical image and the converted second medical image.

* * * * *